(12) United States Patent
Adam

(10) Patent No.: US 7,318,522 B2
(45) Date of Patent: Jan. 15, 2008

(54) CARRYING CASE FOR DENTAL HYGIENE SUPPLIES AND HOLSTER FOR CARRYING CASE

(76) Inventor: Donna Kay Adam, 612 S. Fifth Ave., Des Plaines, IL (US) 60016

( * ) Notice: Subject to any disclaimer, the term of this patent is extended or adjusted under 35 U.S.C. 154(b) by 85 days.

(21) Appl. No.: 10/905,667

(22) Filed: Jan. 14, 2005

(65) Prior Publication Data

US 2006/0157379 A1    Jul. 20, 2006

(51) Int. Cl.
*A61B 19/02* (2006.01)
*B65D 25/22* (2006.01)

(52) U.S. Cl. .................... 206/63.5; 206/369; 220/481; 248/311.2; 248/318

(58) Field of Classification Search ............... 206/63.5, 206/368–369, 509–511, 570–572, 581, 815; 132/308–316; 220/480–481; 248/311.2, 248/318
See application file for complete search history.

(56) References Cited

U.S. PATENT DOCUMENTS

| | | | | |
|---|---|---|---|---|
| 942,714 | A * | 12/1909 | Cromwell | .................... 220/480 |
| 3,116,849 | A * | 1/1964 | Brewer et al. | ........... 248/311.2 |
| 3,205,521 | A * | 9/1965 | McCaughey et al. | ........ 132/308 |
| 3,966,076 | A * | 6/1976 | Kroger et al. | ............... 220/835 |
| 3,977,743 | A | 8/1976 | Harris | |
| 4,527,574 | A | 7/1985 | Manfredi | |
| 5,086,916 | A * | 2/1992 | Gray | ........................ 132/308 |
| D324,952 | S * | 3/1992 | Berland | .................... D3/203.1 |
| 5,095,924 | A | 3/1992 | Stanfield | |
| 5,152,307 | A | 10/1992 | Schlaszus et al. | |
| 5,170,907 | A * | 12/1992 | Sakai | ........................ 220/481 |
| 5,215,193 | A * | 6/1993 | Dennis | ....................... 206/581 |
| 5,595,302 | A * | 1/1997 | Maydwell et al. | .......... 206/579 |
| 5,699,925 | A * | 12/1997 | Petruzzi | ...................... 206/511 |
| 6,206,192 | B1 * | 3/2001 | Winstead et al. | ........... 206/572 |
| 6,220,253 | B1 | 4/2001 | Wright | |
| 6,484,732 | B1 | 11/2002 | Simister | |
| 6,526,991 | B2 | 3/2003 | Bodwalk | |
| 6,776,296 | B2 | 8/2004 | Herren | |
| 2004/0107524 | A1 | 6/2004 | Kazmi | |

* cited by examiner

*Primary Examiner*—Bryon P Gehman

(57) ABSTRACT

The invention concerns two distinct components related to dental hygiene. The first is a dental hygiene carrying case that has been specially designed to hold various dental supplies. The second part of the invention is a holster unit that is used to support (hold) the carrying case.

1 Claim, 6 Drawing Sheets

CARRYING CASE FOR DENTAL HYGIENE SUPPLIES AND HOLSTER FOR CARRYING CASE

BACKGROUND OF THE INVENTION AND DESCRIPTION OF PRIOR ART

The prior art includes primarily carrying cases for toiletries which include dental, as well as other general hygiene supplies and smaller travel kits for dental supplies. The present invention is totally unique from these types of inventions in its form and functionality. First I will describe the prior art because it has a bearing on the dental hygiene field, then I will explain how nothing in the prior art comes close to the current invention's form and function. Each of the inventions in the prior art has at least one element of the current invention, but none has enough elements to even compare to the current invention which makes the current invention a totally new dental hygiene carrying system.

There are several previous inventions related to carrying cases for toiletries in general and some have compartment that are large enough to hold dental hygiene supplies. Inventions of these types include Stanfield U.S. Pat. No. 5,095,924 which includes a carrying case and allows ease of opening the case and keeps the objections stationary. This invention is not specific to dental supplies however. Also, this invention allows little flexibility for the user to define which supplies they choose. Also Schlaszus U.S. Pat. No. 5,152,307 is another example of a toiletry case with various compartments that is good for travel. It is not specific to dental care, nor does it give flexibility to the user as the compartments are preset.

Simister U.S. Pat. No. 6,484,732 is an example of a carrying case that is designed specifically for dental hygiene supplies. Although it has compartments and some flexibility for the user; it is shaped more like a bottle which makes it distinctly different from the current invention as the current invention has a box-like shape. Simister U.S. Pat. No. 6,484,732 has a shape that makes it easier to hold than some other inventions; however the present invention has a revolutionary design that makes it easy to carry and adds the element of organization that is lacking in Simister U.S. Pat. No. 6,484,732.

Another carrying case designed specifically for dental supplies is Wright U.S. Pat. No. 6,220,253. This case has several sections for dental supplies but does not seem to accommodate the types of dental supplies currently on the market with the various compartments. Also Wright U.S. Pat. No. 6,220,253 does not have the design components of the present invention which make it easy to carry. These are specific features the present invention has overcome.

Also, in the last several years, patents have been submitted that try to store the supplies in as small a unit as possible, such as Bodwalk U.S. Pat. No. 6,526,991 claiming a dental hygiene kit that is the size of a writing pen and also US Patent Application US2004/0107524 Kazmi which also has a latch so that it can attach to a shirt pocket. Manfredi U.S. Pat. No. 4,527,574 claims a small travel size compact kit. These patents try to make the case small enough to fit into small spaces such as a purse or even a pocket for traveling, which are good goals for their particular inventions. The present invention does not seek to fit into this type of design and is totally unique in its construction. The current invention can be used as a travel kit, but that is not its primary function, therefore it does not seek to make the case small, but rather seeks to provide ample space for dental hygiene supplies and make the process of teeth brushing organized and enjoyable by providing elements of organization when the user stores the carrying case in the holster device. The present invention is not seeking to provide any unit that is so small that the user would even call it a compact travel kit. The user may choose to travel with the present invention even though it is larger than most travel kits, because the user may like the other features of the present invention as mentioned in the claims.

Lastly, in the prior art there are some units that have components that attach to a wall. These types of inventions allow sanitation of toothbrushes and allow organization such as U.S. Pat. No. 6,776,296 that holds four toothbrushes on a wall unit and Harris U.S. Pat. No. 3,977,743 that holds a single toothbrush and also attaches to a wall unit and can be removed for travel. These patents offer the organization for single toothbrushes and allow the user to get their toothbrush easily, but it lacks the organization of the entire supplies needed to brush teeth that the present invention supplies. These types of inventions also do not come near to having elements of the present invention, but are worth mentioning in prior art.

No one, to the inventor's knowledge, has combined a carrying case that has a stationary holster that can be placed on a wall, wall unit, locker, desk or desktop, or other such place the user determines and is made specifically for the carrying case for the dental hygiene carrying case. There were many attempts to find this prior art, but not could be found.

In the prior art there are dental kits and dental cases that seek to meet various objectives but none that provide the user with a carrying case with ample room for their dental supplies, with the layout and design components that have been attained in the present invention, along with a holster unit to allow the user to attach the carrying case to their designated space. The components of the present invention make it unique from all the prior art in its form and function such that it is considered a new and unique carrying case and holster system.

SUMMARY OF THE INVENTION

The objects below are presented in summary fashion and it is the intention of the inventor that these are to be read with the entire patent document and that the document is to be taken as a whole.

The current invention overcomes the difficulties in the prior art by providing a dental hygiene carrying case that is specific for dental supplies and holds the supplies in a relatively stationary position within the case by using walls that go to the top of the case when the case is shut. The case provides the aforementioned compartments yet gives flexibility to the user for their own dental supplies as there are a variety of supplies on the market.

Another object of the carrying case is to provide a design which allows the user to easily carry the case by providing a size, an arched bottom element and a rounded top that allows the user to easily carry the unit.

Another object of the invention is to provide a holster unit for the carrying case to allow the user to be organized with their dental supplies. The holster unit is attached to a place designated by the user and remains stationary in that designated space. The user will take the carrying case out of the holster, use the supplies, and return the carrying case to the holster when they are done. This allows the user to have a place designated for the supplies and have them readily available for use.

The overall objective of the invention is to promote better oral hygiene by providing an improved carrying case and holster system for teeth brushing for use in the workplace, school, home and travel. It is the objective of the current invention that the user will use the carrying case and holster on a daily basis and not be limited to travel, although it is also suitable for travel.

DETAILED DESCRIPTION OF THE INVENTION

The present invention has two distinct components.

Figure 1:
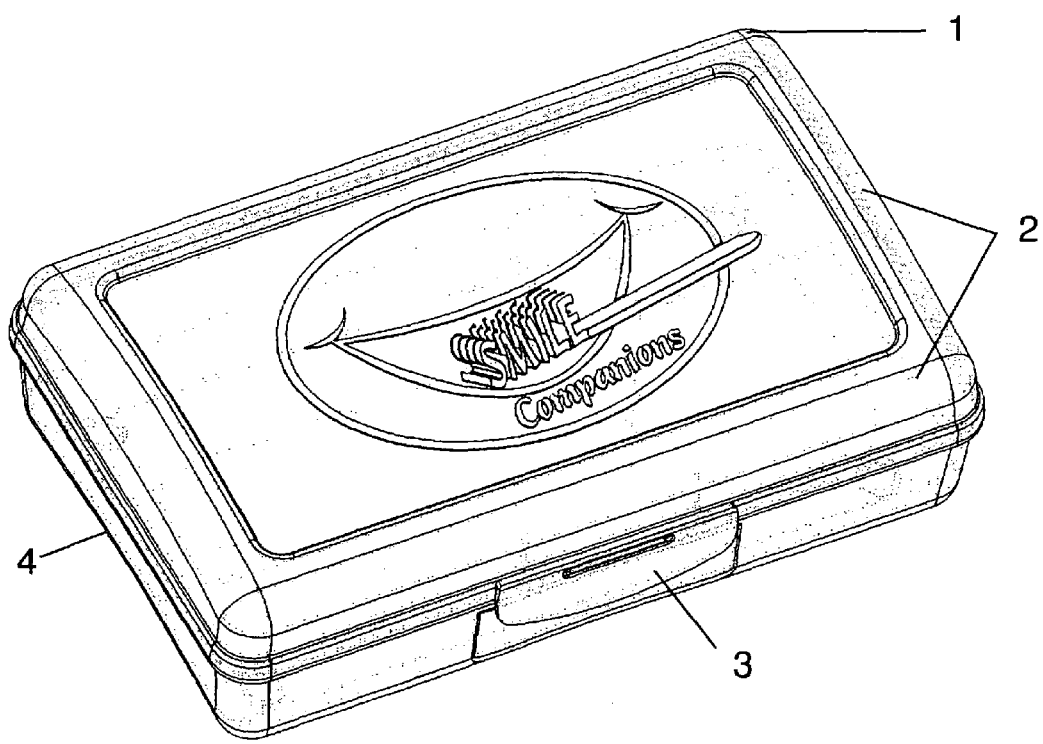
FIG. 1 is a view of the "Carrying Case for Dental Hygiene Supplies" showing the box closed. This view shows the rounded edge (1) on the top, the hinge latch (3) and the overall look of the box.
Figure 2:
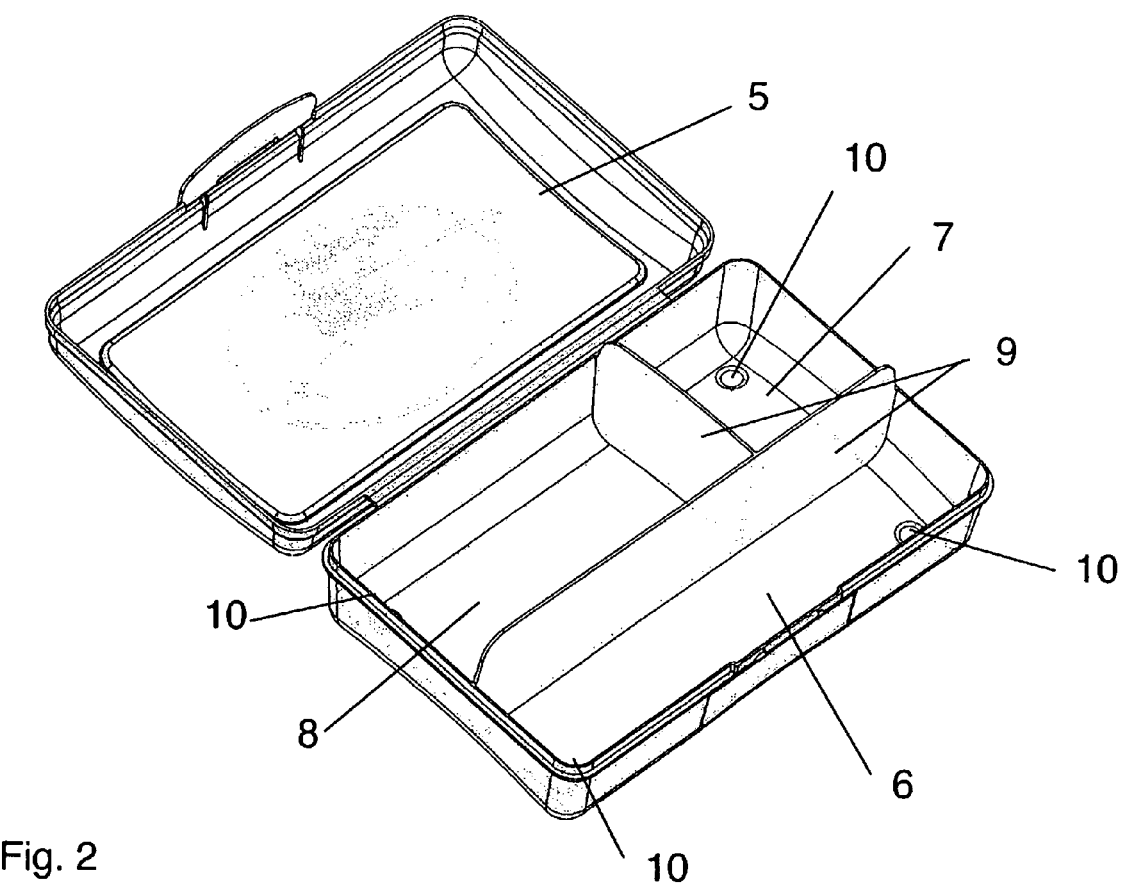
FIG. 2 is a view of the "Carrying Case for Dental Hygiene Supplies" showing the box open. This view shows the compartments (6, 7, 8) and the elongated walls (9) which keep the supplies in a semi-stationary manner.
Figure 6:
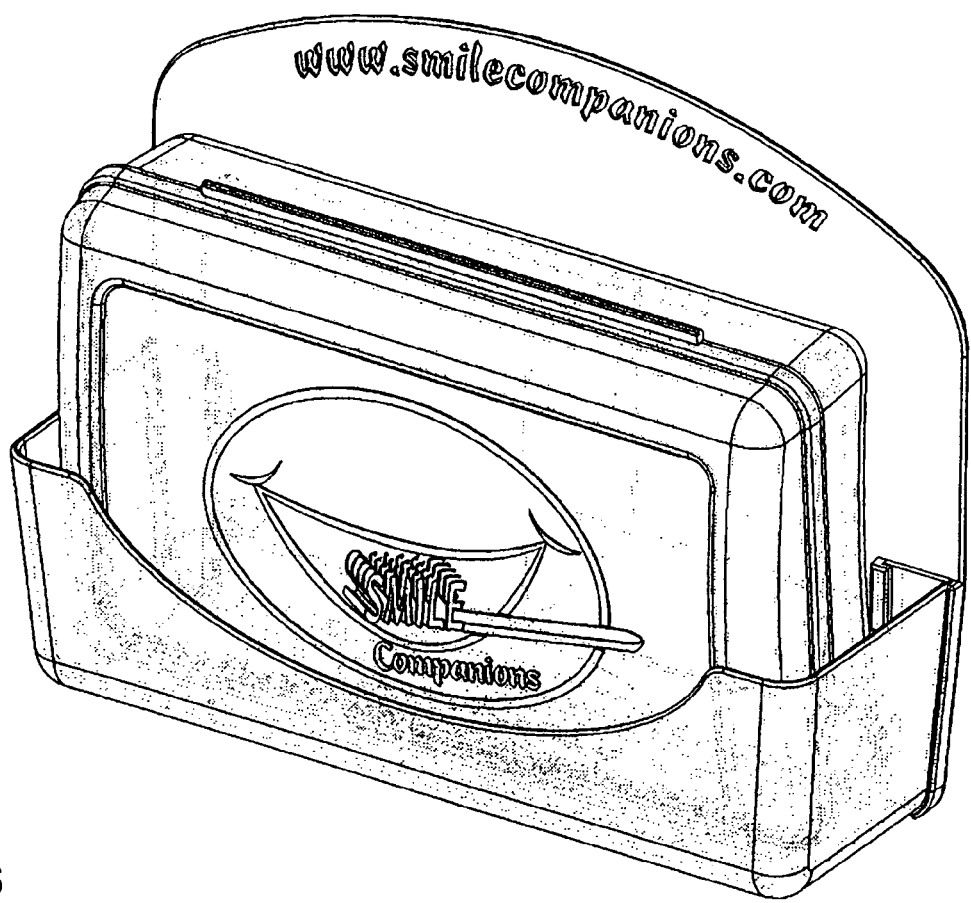
FIG. 6 is a front view of the "Carrying Case for Dental Hygiene Supplies" placed inside of the "Holster for Carrying Case for Dental Hygiene Supplies".

The first of the two components of the invention is a carrying case for dental hygiene supplies. See FIGS. 1, 2, 6. The carrying case has compartments (6, 7, 8) that have been specially designed to accommodate dental hygiene supplies. The compartment walls (9) are elongated upward such that when the lid (5) is closed the supplies cannot move to the other compartments, keeping the supplies relatively stationary in their space. There are three separate compartments (6, 7, 8) that are designed for various dental supplies. The longest section (6) will hold a toothbrush and tube-style toothpaste. The smallest compartment (7) is designed to hold floss and a collapsible rinsing cup. The middle size compartment (8) is designed to add flexibility to the box. The middle size compartment (8) will hold toothpaste that is not of the tube-style and other dental supplies the user will designate such as rinse, mouthwash and toothpicks. The user will take the supplies out of the case to use them and then put them back for storage. This case has ample room for the user and is made convenient for travel or use at home, work and school. The case has a hinge which allows the case to be conveniently opened (latch 3) by the user to use the supplies. The case also has design elements such as a rounded edge (1) on the top, an arched bottom (4), and a convenient size which make it easy to carry. The overall size of the case is approximately 7.9 inches long by 5 inches wide and 2 inches deep.

Figure 3:
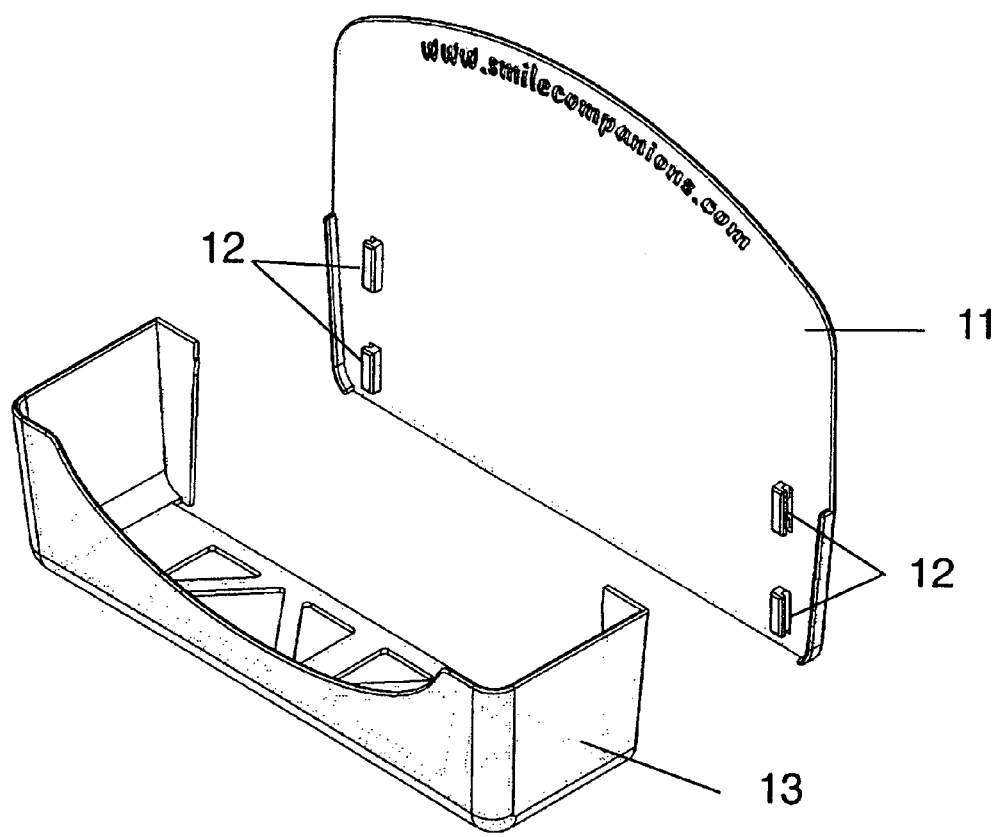
FIG. 3 is a view of the "Holster for Carrying Case for Dental Hygiene Supplies" showing the unit is made of two parts (11, 13) that snap (12) together.
Figure 4:
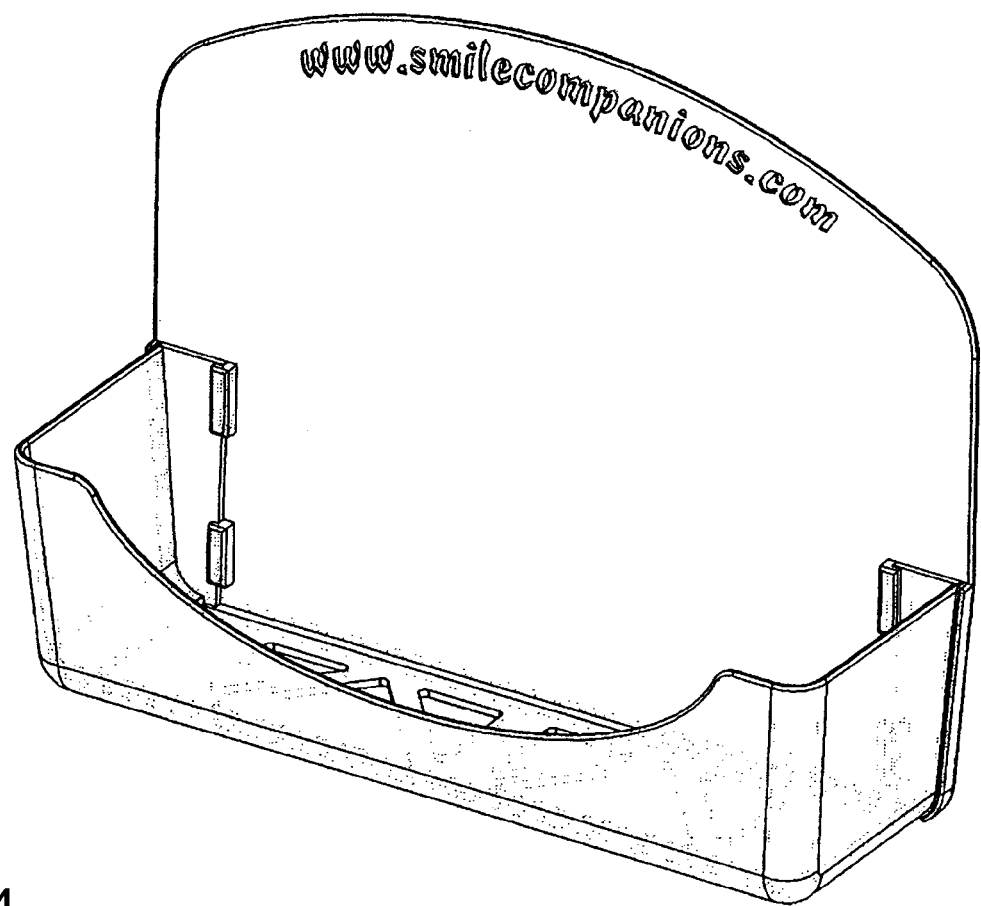
FIG. 4 is a front view of the "Holster for Carrying Case for Dental Hygiene Supplies".
Figure 5:
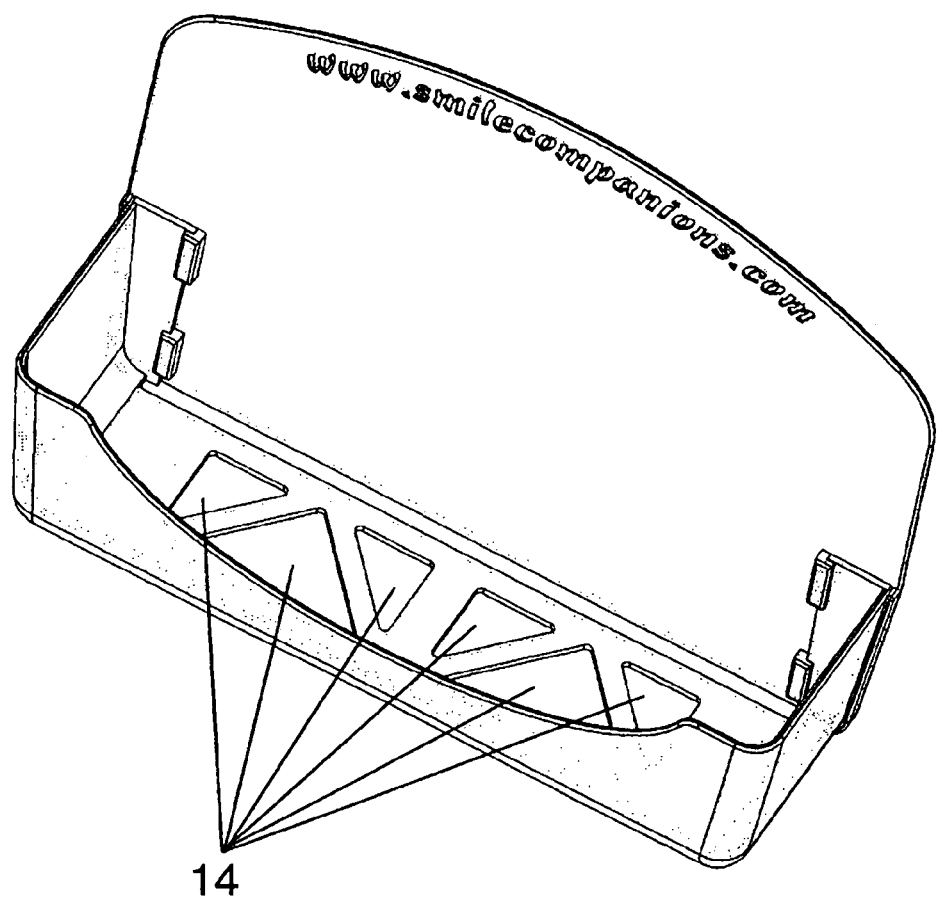
FIG. 5 is a top view of the "Holster for Carrying Case for Dental Hygiene Supplies" showing the openings at the bottom.

The second of the two components of the invention is a "Holster for Carrying Case for Dental Hygiene Supplies." (See FIGS. 3, 4, 5) The holster serves the purpose of storing the dental hygiene carrying case so that the user is more organized with their dental supply carrying case. The holster can also serve as a reminder for teeth brushing, as the user can place the holster in an area designated by the user such that the holster can be viewed and is a reminder to brush their teeth and have better dental hygiene overall.

The holster is designed to attach to a wall, wall unit, locker, cubicle, desk or desktop, inside a drawer or cabinet, or other such places as a user would deem convenient for storing their dental supplies. The holster is designed to attach to these various places using various methods not limited to mounting tape, hook and loop devices, glue or nails. A "Carrying Case for Dental Hygiene Supplies" (as described in the first part of the invention) is placed in the holster for storage when the dental supplies are not being used. When the user would like to use the supplies or would like to remove the carrying case for travel, the carrying case is taken out of the holster. The holster is specifically designed to hold the carrying case (as described in the first part of the invention), and is designed to allow the carrying case to be easily placed in or taken out of the holster. In addition, the bottom of the holster has openings (14) that serve two purposes, the first of which is to allow for any moisture that has collected on the carrying case to ventilate and the second purpose of the holes at the bottom of the holster is to allow the user, if they wish, to push their fingers through the bottom of the holster in an upward motion to help remove the carrying case from the holster. The overall size of the holster is approximately 9 inches wide, 7 inches tall and 2.8 inches deep at the base to hold the carrying case.

Case is subdivided into compartments (6, 7, 8) specifically designed to hold dental supplies.

The compartments (6, 7, 8) are designed to hold specific supplies, but include some flexibility for the user to determine which dental supplies the user would like to include.

The compartments are designed to have flexibility for a variety of sizes of toothbrushes, toothpaste, floss, rinse and rinsing cup. This box is designed to accommodate a wide variety of dental supplies. The user will determine what supplies are needed for their particular needs and may also include other supplies not mentioned.

The sides (9) of the compartments (6, 7, 8) extend high enough such that when the box is closed the dental supplies will not move from one compartment to another.

The case is designed with three compartments (6, 7, 8) that hold various dental supplies.

The longest section (6) will hold a toothbrush and tube-style toothpaste. The smallest compartment (7) is designed to hold floss and a collapsible rinsing cup. The middle size compartment (8) will hold toothpaste that is not of the tube-style and other dental supplies the user will designate such as rinse, mouthwash and toothpicks. The user will take the supplies out of the case to use and then put them back for storage.

The box has design components that make the box easy to hold and to carry.

Two of the special design components are a rounded edge (1) on the top (5) of the box which aids in making the case easy to hold and a slight arch (4) on the bottom of the box which in conjunction with the rounded top (5), makes the case easy to carry.

The bottom of the box has four small rounded dots (10) that serve as feet. These dots (10) help to raise the box, such that when it sits on a washbasin or surface, is easy to remove from the surface.

The case has a hinge (FIG. 2). which allows the user to open the box (latch 3) to conveniently remove the dental supplies when needed.

The case is designed to have ample room for the user's dental supplies and is made convenient for travel or use at home, work and school. The overall size of the case is approximately 7.9 inches long by 5 inches wide and 2 inches deep.

A holster unit (FIGS. 3, 4, 5) for holding a carrying case for dental supplies.

The holster unit can attach semi-permanently or permanently to surfaces such as walls, wall units, desk, desktops, lockers, or other places the user may choose using various methods for attachment including mounting tape, hook and loop supplies, nails, glue or various other mounting options.

The carrying unit for dental supplies is removed from the holster when the user goes to the washroom to brush their teeth, travels, or otherwise chooses to remove the carrying case for their teeth brushing needs.

The holster unit serves the purpose of holding the "Carrying Case for Dental Hygiene Supplies." The overall size of the holster is approximately 9 inches wide, 7 inches tall, and 2.8 inches deep at the base to hold the carrying case.

The holster unit serves the purpose of overall helping the user to keep their dental supplies organized and out the way once the user has the supplies, and it keeps them out of the way until the user chooses to use them again.

The holster unit serves the purpose of reminding the user to brush their teeth (as the user determines a place for the holster that, at the user's option, can be placed in an area within eyesight so that the user is reminded to brush their teeth especially after meals. The holster unit can also be placed in hidden areas, such as in a cabinet, drawer, or other place if the user so decides.

The holster unit has holes (14) in the bottom, shaped as triangles, which serve the purpose of allowing for any moisture that may be on the carrying case to ventilate.

The holes (14) in the bottom of the holster unit allow the user, if they wish, to push their fingers through the bottom of the holster to push the carrying case upward to help remove the carrying case from the holster unit.

What is claimed is:

1. A carrying case and holster for dental hygiene supplies, comprising a hand-carriable carrying case having a top portion and a bottom portion that are hinged together and are moveable about the hinge between an open position and a closed position, the bottom portion having a plurality of compartments containing personal dental hygiene supplies in compartmental relationships in the closed position; and a stationary holster sized to snuggly and removably receive the carrying case when in the closed position, an openable side of the carrying case opposite the hinge resting against a bottom-most portion of the holster, wherein the holster is provided with openings in its portion bottom-most to facilitate moisture evaporation and the release of the carrying case from the holster.

* * * * *